(12) United States Patent
Clement

(10) Patent No.: US 8,465,527 B2
(45) Date of Patent: Jun. 18, 2013

(54) VERTEBRAL OSTEOSYNTHESIS EQUIPMENT

(75) Inventor: Jean-Luc Clement, La Colle sur Loup (FR)

(73) Assignee: Medicrea International, Neyron (FR)

( * ) Notice: Subject to any disclaimer, the term of this patent is extended or adjusted under 35 U.S.C. 154(b) by 128 days.

(21) Appl. No.: 12/991,140

(22) PCT Filed: May 26, 2009

(86) PCT No.: PCT/IB2009/052202
§ 371 (c)(1), (2), (4) Date: Jan. 24, 2011

(87) PCT Pub. No.: WO2009/144663
PCT Pub. Date: Dec. 3, 2009

(65) Prior Publication Data
US 2011/0112581 A1 May 12, 2011

(30) Foreign Application Priority Data
May 27, 2008 (FR) ...................................... 08 02863

(51) Int. Cl.
*A61B 17/70* (2006.01)
(52) U.S. Cl.
USPC ........................................................ 606/264

(58) Field of Classification Search
CPC ........................................................ A61B 17/70
USPC ................. 606/246–250, 253, 256, 263, 264, 606/266, 267, 272, 276, 301, 74
See application file for complete search history.

(56) References Cited

U.S. PATENT DOCUMENTS 5,454,812 A 10/1995 Lin
6,641,584 B2 * 11/2003 Hashimoto et al. ........... 606/330

FOREIGN PATENT DOCUMENTS

FR 2 816 196 5/2002
FR 2 890 850 3/2007

* cited by examiner

*Primary Examiner* — Eduardo C Robert
*Assistant Examiner* — David Comstock
(74) *Attorney, Agent, or Firm* — Oliff & Berridge, PLC

(57) ABSTRACT

Equipment at least one anchoring assembly including a hook integral with a body, this body being passed through by a hole and capable of being connected to connection means making it possible to connect the anchoring assembly to a connection bar for connecting a series of vertebrae. The anchoring assembly has a continuous flexible ligament able to be engaged in the hole and to form a loop allowing the engagement of the ligament around a structure of a vertebrae or mounted on a vertabrae, and has stop means making it possible to immobilize this ligament in relation to the body.

13 Claims, 3 Drawing Sheets

VERTEBRAL OSTEOSYNTHESIS EQUIPMENT

The present invention concerns a vertebral osteosynthesis equipment.

An equipment of this type generally comprises one or two connecting bars making it possible to connect a series of vertebrae to each other and anchoring assemblies of these connecting bars to the vertebrae, with hooks or pedicle screws. This equipment can also comprise crosspieces which transversely connect two connecting bars increasingly closely in order to maintain them in relation to each other.

One existing type of anchoring assembly comprises two antagonistic hooks connected to each other by a connecting rod, a first hook of which comprises a body passed through by the connecting rod and is connected to connection means allowing the connection of this first hook to a connecting bar. In an anchoring assembly known through French patent application No. FR 2 816 196, in the applicant's name, the body of said first hook comprises a hole for the passage of the connecting rod, this hole having an oblong section on the side turned toward the second hook; this oblong section of the hole allows travel of the connecting rod in a plane and as a result increases the possibilities for positioning of this second hook in relation to the first hook. The connecting rod is threaded and, after having passed through the body of the first hook, receives a nut making it possible to connect it to the first hook. This nut makes it possible, through its tightening, to bring the second hook closer to the first hook.

This known equipment is satisfactory in practice, but is not, however, free of all drawbacks. Indeed, this equipment has limits as to its positioning possibilities on vertebrae and is not adapted to certain types of assembly. Furthermore, the nut can, depending on the position of the anchoring assembly on the vertebrae, be more or less difficult to access, making the tightening operation of this nut delicate. Moreover, any risk of play of the anchoring assembly appearing in relation to the vertebrae is not excluded with this equipment.

The aim of the present invention is to provide an anchoring assembly of the aforementioned type, resolving the aforementioned drawbacks.

Documents FR 2 890 850 and U.S. Pat. No. 5,454,812 describe other equipments of the same type, having similar drawbacks.

The equipment concerned by the invention comprises, in a known manner, at least one anchoring assembly including a hook integral with a body, this body being passed through by a hole and capable of being connected to connection means making it possible to connect the anchoring assembly to another part comprised by the equipment, in particular a connection bar of a series of vertebrae.

According to the invention, the anchoring assembly comprises a continuous flexible ligament able to be engaged in said hole and to form a loop allowing the engagement of the ligament around a structure of a vertebrae or mounted on a vertabrae, and comprises stop means making it possible to immobilize this ligament in relation to said body.

The ligament can thus, instead and in place of said second hook according to the prior art, be engaged directly around a bone part of a vertebra or a catch portion implanted on this vertebra and act in cooperation with said hook to ensure maintenance of the anchoring assembly on this vertebra or on several vertebrae; once this engagement is done, the anchoring assembly is immobilized on the treated vertebra(e) by tensioning the ligament in relation to the body of the hook by traction on said ligament, then stopping of the ligament in relation to the body, using stop means, in this tensioned state.

The ligament, due to its flexibility and continuity, allows adaptation of the anchoring assembly to all implantation positions which may arise, making the equipment according to the invention adapted to all types of assembly. The anchoring assembly also does not comprise nuts, thereby eliminating the problems related to the difficulty of tightening the nut as well as the risk of loosening of this nut resulting in the appearance of play of the anchoring assembly in relation to the vertebrae.

The ligament can be in the form of a lasso, i.e. comprise an eyelet at one end, through which the other end of the ligament can be engaged and through which the ligament is capable of sliding.

This engagement is done after the ligament has been engaged around a bone part; the loop thus formed is then adjusted around this bone part, then the single strand formed by the ligament is engaged through the body of the hook.

The ligament can also form a loop on one side of the hook, and thus comprise two strands capable of being engaged through the hole of the hook.

These two strands are stopped by said stop means after having been tensioned.

These stop means can assume the form of a block of material able to be permanently deformed, in particular crimped, on the ligament.

According to one possible embodiment of the invention, these stop means comprise:

an opening arranged in said body substantially perpendicular to the axis of said hole, communicating with this hole, and a tightening member able to be engaged in this opening until it bears against the ligament and able to be tightened in order to immobilize the ligament in the hole.

Thus, in the equipment according to the present invention, the tightening member intended to immobilize the ligament is placed directly in the body of the hook, so as to bear against the ligament and squeeze the latter part against the body of the hook. This tightening member is easily accessible regardless of the position of the anchoring assembly in relation to the treated vertebrae, which noticeably facilitates the placement of this anchoring assembly on these vertebrae and makes it possible to achieve complete immobilization of the ligament in relation to the hook.

The tightening member advantageously comprises a flat surface intended to bear against the ligament.

This flat surface allows an extended tightening surface of the ligament, ensuring good immobilization of the ligament in relation to the tightening member and preventing a risk of localized deterioration of this ligament.

The ligament can have a circular or flat transverse section. When it forms two strands intended to go through said hole and it has a circular transverse section, this hole is preferably arranged such that the two strands can be engaged therein side by side. When the ligament forms two strands intended to go through said hole and it has a flat transverse section, this hole is preferably arranged such that the two strands can be engaged therein one on top of the other.

Said tightening member can be independent of said means for connecting the body of the hook to said other part (connecting bar) comprised by the equipment; preferably, however, this tightening member is connected directly to these connection means, for which it enables the assembly of the hook on the body.

The manufacture of the equipment according to the invention, and its placement on vertebrae, are thus facilitated.

Said connection means can comprise a part for assembling the hook to said other part (connecting bar), which is not articulated in relation to the body of the hook. An unarticulated assembly piece of this type is generally called "monoaxial". In this case, said tightening member is advantageously formed by a portion of this assembly part, integral therewith.

Said connection means can also comprise a part for assembling the hook to said other piece (connecting bar) of the equipment, which is articulated in relation to the body of the hook. An articulated assembly piece of this type is generally called "polyaxial". In this case, said tightening member is formed by a connecting piece independent of said assembly piece, connected by articulation thereto.

The body of the hook and/or said tightening member can comprise at least one rough surface at their contact areas with the ligament, able to oppose the sliding of the ligament in relation to the body and/or the tightening member when this member is tightened. The rough nature of this surface can in particular result from knurling.

According to one preferred embodiment of the invention,
said opening arranged in said body is formed by a tapped bore, and
said tightening member comprises a threaded portion enabling it to be screwed in this tapped bore.

When the equipment comprises a polyaxial assembly part, said connecting piece, which forms said anchoring member, includes this threaded portion and comprises an engaging zone making it possible to take hold of said threaded portion in order to screw it into the tapped bore.

The invention will be well understood, and other characteristics and advantages thereof will appear, in reference to the appended diagrammatic drawing illustrating, as non-limiting examples, two possible embodiments of the equipment it concerns.

FIGS. 1 to 4 illustrate an anchoring assembly 1 which is part of a vertebral osteosynthesis equipment.

Figure 1:
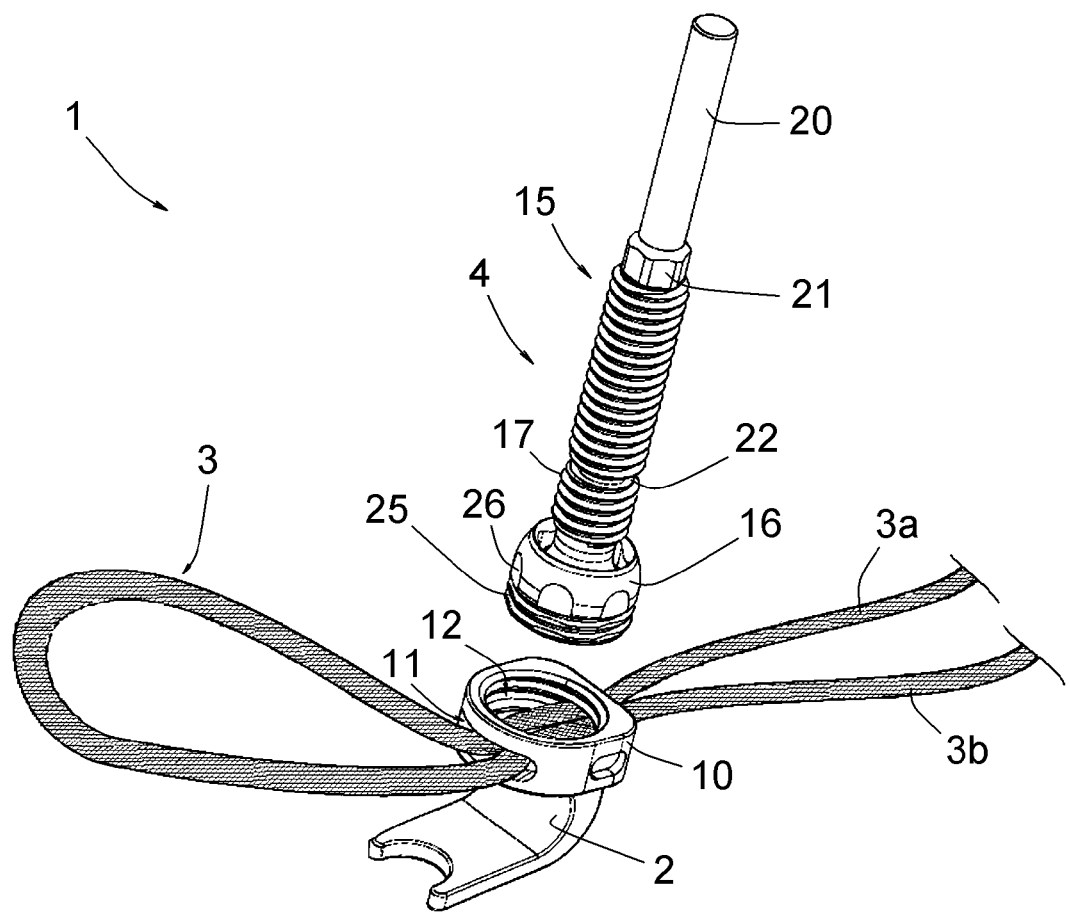
FIG. 1 is a perspective view of this equipment according to a first embodiment, before assembly.

This vertebral osteosynthesis equipment comprises, as is well known, one or two connecting bars (not shown) making it possible to connect a series of vertebrae to each other and several assemblies 1 making it possible to anchor these connecting bars to the vertebrae. This equipment can also comprise crosspieces which transversely connect two connecting bars increasingly closely in order to maintain them in relation to each other.

Said bars and crosspieces are well known in themselves and are therefore not shown in the drawings, or particularly described.

As shown by the figures, an anchoring assembly 1 comprises a hook 2, a ligament 3 and a connection sub-assembly 4. The hook 2 and the ligament 3 are intended to be engaged simultaneously around bone parts 100, 101 of one or several vertebrae, in particular at a plate of one of these vertebrae, in order to allow this assembly 1 to be connected to this or these vertebra(e). This hook 2 and/or this ligament 3 could also be engaged around catch portions implanted in one and/or the other of the vertebrae and integral therewith.

The hook 2 is integral with a body 10 comprising a hole 11 which goes all the way through it, in which the ligament 3 is intended to be engaged.

The hook 2 is made up of a curved leg, the base of which, connected to a surface of the body 10, is curved, and opens on one side of this body 10.

The body 10 comprises a tapped bore 12, extending therein from the surface of this body opposite that comprising the hook 2, until it communicates with the hole 11.

The latter part goes through the body 10 according to the thickness thereof. In the illustrated example, it is arranged along a direction extending from said side on which the hook 2 opens up to the opposite side of the body 10. It has, seen along its axis, a flat, oblong-shaped transverse section.

In the embodiment shown in FIG. 1, the ligament 3 has a circular transverse section and is able to form a loop ending with two strands 3a, 3b; the hole 11 is arranged such that these two strands 3a, 3b can be engaged therein side by side.

Figure 2:
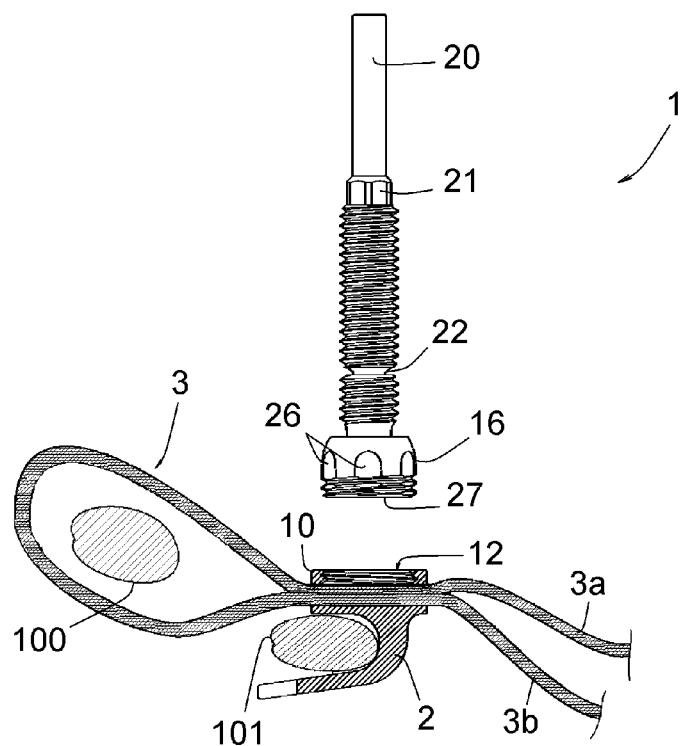
FIG. 2 is a side view, partially in cross-section, during a step for placement on a vertebra.
Figure 3:
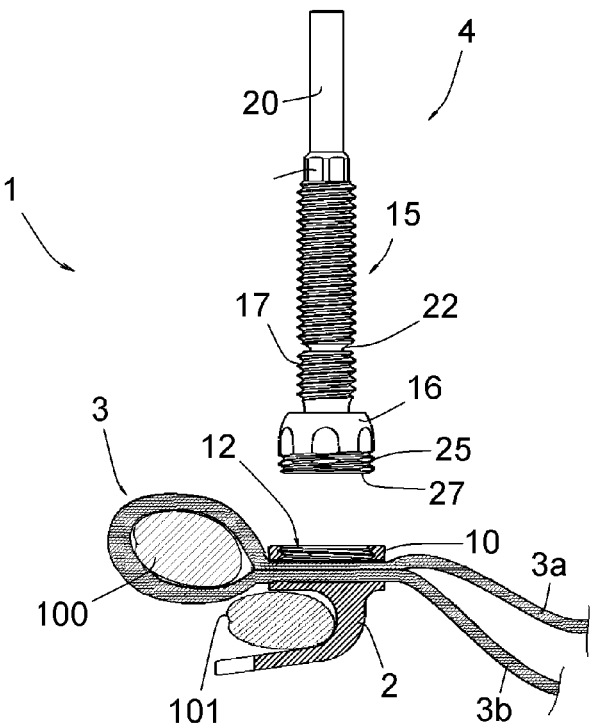
FIG. 3 is a view similar to FIG. 2, during a following placement step.
Figure 4:
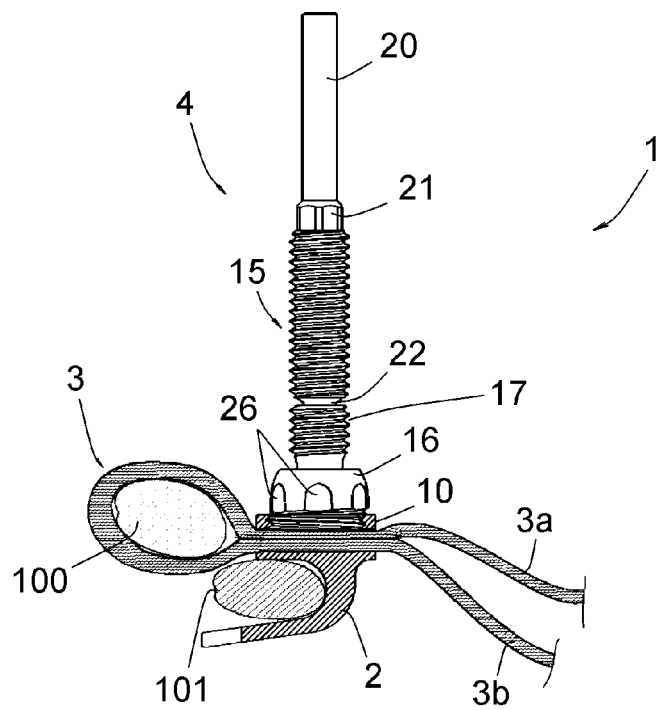
FIG. 4 is a view similar to FIG. 3, after placement.

In the embodiment shown in FIGS. 2 to 4, the ligament 3 has a flat transverse section and the hole 11 is arranged such that the two strands 3a, 3b can be engaged therein one on top of the other.

The assembly formed by the hook 2 and the body 10, and the connection sub-assembly 4 are made in a biocompatible metal such as titanium or a titanium alloy; the ligament 3 can be made up of a braid of polyester wires.

The connection sub-assembly 4 comprises, in the illustrated example, a threaded slug 15 and a connecting piece 16 articulated to each other. This articulation is done using a terminal spherical portion comprised by the slug 15 and a spherical cavity for receiving this terminal portion arranged in the connecting piece 16. To achieve the connection of this slug 15 and this piece 16, the connection piece 16 can in particular comprise a peripheral wall able to be folded down against the spherical portion of the slug 15 by deformation around this spherical portion, like a crimping.

The slug 15 comprises a threaded portion 17 intended, as is known, to receive a connector link (not shown) of a connecting bar as previously mentioned, then to receive a nut (not shown) for tightening this link around this connecting bar, the link resting against the peripheral wall of the connecting piece 16. This link and this nut, being well known in themselves, are not particularly shown in the drawings or described, and one can refer to the aforementioned French patent application No. FR 2 816 196 for an example of embodiment of a link and a nut of this type.

The slug 15 also comprises a smooth proximal portion 20 making it possible to facilitate the engagement of the link and the nut thereon, a facetted portion 21, making it possible to immobilize this slug 15 in rotation during screwing of said nut, and a portion 22 with a smaller section, which can be broken after tightening of the nut against the link.

The connecting piece 16 is, as appears in the figures, intended to be screwed into the tapped bore 12. To this end, it comprise a threaded portion 25 allowing its screwing in this bore 12 and a plurality of facets 26 on its periphery allowing its engagement using a suitable tool and its driving in rotation. The connecting piece 16 also comprises a flat distal surface 27 intended to bear against the ligament 3 during its screwing in the bore 12.

As is understood, the anchoring assembly 1 is assembled by engaging a strand 3a of the ligament 3 in the hole 11, then screwing the connecting piece 16 in the tapped bore 12, without tightening.

As shown by FIG. 2, this anchoring assembly 1 is placed by engaging the ligament 3 around the concerned bone part 100, engaging the other strand 3b of this ligament 3 in the hole 11, then engaging the hook 2 on the concerned bone part 101. The loop formed by the ligament 3 is then adjusted around the bone part 100 by traction on one of the strands 3a, 3b, or on these two strands 3a, 3b (cf. FIG. 3), then the connecting piece 16 is tightened, using an appropriate tool, in the bore 12 such that its flat distal surface 27 grips the ligament 3 between it and the body 11.

Figure 5:
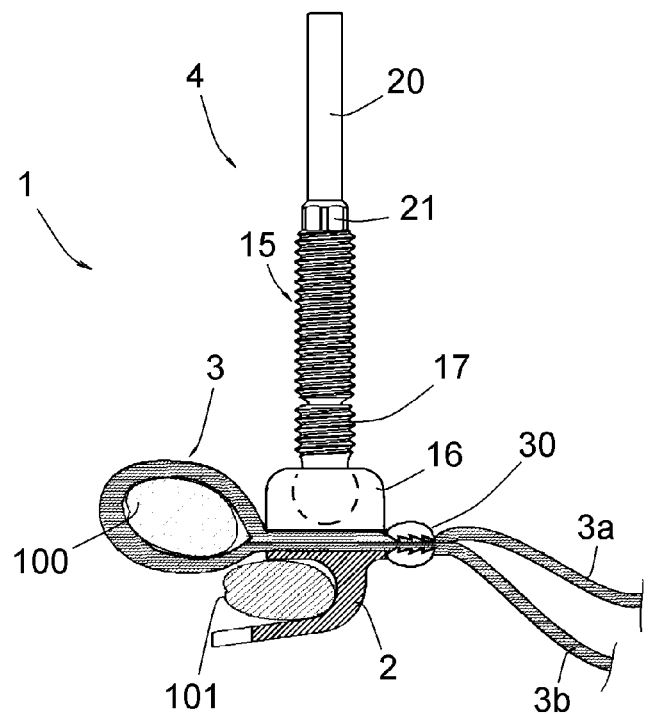
FIG. 5 is a view similar to FIG. 4, according to a second embodiment.

FIG. 5 shows another embodiment of the anchoring assembly 1. The parts or elements already described in reference to FIGS. 1 to 4 which are found identically or similarly in this other embodiment will not be described again and are designated using the same numerical references.

In this embodiment, the connecting piece 16 of the connection sub-assembly 4 is integral with the body 11. Stopping of the ligament 3 is done using a block 30 of material capable of being permanently deformed, in particular crimped, on the ligament 3. This block 30 comprises a conduit for the passage of the strands 3a, 3b and teeth capable of biting into the material of the ligament 3.

The invention provides a vertebral osteosynthesis equipment in which the ligament 3 acts, instead and in place of a hook according to the prior art, in cooperation with the hook 2 in order to ensure maintenance of the anchoring assembly 1 on one or several vertebra(e). Due to its flexibility, this ligament 3 allows adaptation of the anchoring assembly 1 to all implantation positions likely to arise, making the equipment according to the invention suited to all types of assembly.

The connecting piece 16 remains easily accessible regardless of the position of the anchoring assembly 1 in relation to the treated vertebrae, such that the anchoring assembly 1 eliminates the problems of the difficulty of tightening the nut of a equipment according to the prior art and the risk of loosening of this nut resulting in the appearance of play of the anchoring assembly in relation to the vertebrae.

Gripping of the ligament 3 between the surface 27 and the body 11 is done by extended contact zones, allowing complete stopping of this ligament in relation to the hook 2 and eliminating the risk of localized deterioration of this ligament.

The invention has been described above in reference to embodiments provided purely as an example. It goes without saying that it is not limited to these embodiments, but that it extends to all other embodiments covered by the appended claims.

The invention claimed is:

1. A vertebral osteosynthesis equipment comprising:
   at least one anchoring assembly including a hook integral with a body, the body being passed through by a hole and capable of being connected to a connection means that connects the anchoring assembly to another part comprised by the equipment, in particular a connection bar that connects series of vertebrae, wherein
   the anchoring assembly has a continuous flexible ligament capable of engaging in said hole and forming a loop to allow the engagement of the ligament around a structure of a vertebrae or mounted on a vertabrae, and has a stop means to immobilize the ligament in relation to said body; and
   the stop means includes:
      an opening arranged in said body substantially perpendicular to an axis of said hole, and
      a tightening member capable of being engaged in the opening until the member bears against the ligament and is tightened in order to immobilize the ligament in the hole.

2. The equipment according to claim 1, wherein the ligament is in the form of a lasso having an eyelet at one end, through which the other end of the ligament can be engaged and through which the ligament is capable of sliding.

3. The equipment according to claim 1, wherein the ligament forms a loop on one side of the hook, and thus has two strands capable of being engaged through the hole of the hook.

4. The equipment according to claim 3, wherein the ligament has a circular transverse section and in that said hole is arranged such that the two strands can be engaged therein side by side.

5. The equipment according to claim 3, wherein the ligament has a flat transverse section and in that said hole is arranged such that the two strands can be engaged therein one on top of the other.

6. The equipment according to claim 1, wherein the stop means assumes the form of a block of material capable of being permanently deformed, in particular crimped, on the ligament.

7. The equipment according 5 claim 1, wherein the tightening member has a flat surface intended to bear against the ligament.

8. The equipment according to claim 1, wherein the tightening member is connected directly to said connection means, for which it enables the assembly of the hook on the body.

9. The equipment according to claim 8, wherein said connection means has a part for assembling the hook to said other part, which is not articulated in relation to the body of the hook, and in that said tightening member is formed by a portion of the assembly part, integral therewith.

10. The equipment according to claim 8, wherein said connection means also comprises a part for assembling the hook to said other piece of the equipment, which is articulated in relation to the body of the hook, and in that said tightening member is formed by a connecting piece independent of said assembly piece, connected by articulation thereto.

11. The equipment according to claim 1, wherein the body of the hook and/or said tightening member comprise(s) at least one rough surface at their contact areas with the ligament, capable of opposing the sliding of the ligament in relation to the body and/or the tightening member when the member is tightened.

12. The equipment according to claim 1, wherein:
   said opening arranged in said body is formed by a tapped bore, and
   said tightening member has a threaded portion enabling it to be screwed in the tapped bore.

13. The equipment according to claim 12, wherein a connecting piece, which forms an anchoring member, includes said threaded portion and has an engaging zone making it possible to take hold of said threaded portion in order to screw it into the tapped bore.

\* \* \* \* \*